(12) United States Patent
Kim et al.

(10) Patent No.: US 8,467,857 B2
(45) Date of Patent: Jun. 18, 2013

(54) HYPODERMIC VEIN DETECTION IMAGING APPARATUS BASED ON INFRARED OPTICAL SYSTEM

(75) Inventors: Seong Keun Kim, Gwanak-gu (KR);
Seung Min Jin, Yuseong-gu (KR);
Hyung Min Kim, Gwanak-gu (KR); Il Seung Yang, Gangseo-gu (KR); Ki Hoon Jin, Dobong-gu (KR)

(73) Assignee: Seoul National University R & DB Foundation (KR)

( * ) Notice: Subject to any disclaimer, the term of this patent is extended or adjusted under 35 U.S.C. 154(b) by 401 days.

(21) Appl. No.: 12/936,581

(22) PCT Filed: Apr. 11, 2008

(86) PCT No.: PCT/KR2008/002071
§ 371 (c)(1),
(2), (4) Date: Nov. 16, 2010

(87) PCT Pub. No.: WO2009/125887
PCT Pub. Date: Oct. 15, 2009

(65) Prior Publication Data
US 2011/0054327 A1    Mar. 3, 2011

(51) Int. Cl.
*A61B 6/00* (2006.01)

(52) U.S. Cl.
USPC .............................. 600/477; 600/407; 600/473

(58) Field of Classification Search
USPC .......................................... 600/407, 473, 477
See application file for complete search history.

(56) References Cited

U.S. PATENT DOCUMENTS 8,078,263 B2 * 12/2011 Zeman et al. ................. 600/473
2008/0103396 A1 * 5/2008 Johnson et al. ............... 600/477

* cited by examiner

*Primary Examiner* — Unsu Jung
*Assistant Examiner* — Joel Lamprecht
(74) *Attorney, Agent, or Firm* — Fish & Associates, PC

(57) ABSTRACT

The present invention is to provide a hypodermic vein detection imaging apparatus capable of visualizing a vein under the skin. The hypodermic vein detection system according to the present invention comprises a hypodermic vein detection imaging apparatus (10) comprising a dome-shaped holder (12), a plurality of infrared light sources (11) arranged at a uniform interval in a circumferential direction on the inner surface of the dome-shaped holder (12), a motor driving unit (13) for rotating the dome-shaped holder (12), teeth (14) meshing with the motor driving unit and formed on the dome-shaped holder (12), an optical zoom lens (15) positioned at the center of the top of the dome-shaped holder, an infrared transmitting filter (16) for filtering light transmitted through the optical zoom lens (15), a first image detector (17) receiving light filtered by the infrared transmitting filter (16), and an image display device (10) for visualizing digital image information obtained by the first image detector (17).

6 Claims, 6 Drawing Sheets

(a)

(b)

HYPODERMIC VEIN DETECTION IMAGING APPARATUS BASED ON INFRARED OPTICAL SYSTEM

TECHNICAL FIELD

The present invention relates to a device for obtaining digital image information of a vein under the skin by using light sources such as an infrared source, particularly to a device for visualizing an image on a display panel in real time by illuminating the skin with infrared light that has geometrically uniform intensity distribution and is radiated from arranged infrared sources such as infrared emission diodes (infrared LEDs) and receiving the light reflected therefrom into an image detector such as a digital camera.

BACKGROUND ART

Publications such as WO96/036273 (Nov. 21, 1996), WO04/093672 (Nov. 4, 2004), and WO04/080276 (Sep. 23, 2004), etc. describe related technology. WO96/036273 and WO04/093672 disclose basic operation principle for visualizing the structure of a hypodermic vein, the types of usable light sources, and detectors. The publications describe a similar method to the present invention, a method of illuminating the skin with light ranging from ultraviolet to infrared by using the corresponding light sources, filtering the reflected or transmitted light by using a filter with a narrow transmission band, and visualizing the image by using various detectors and using a goggle or a projector. All of the publications report that light in the near-infrared region, which penetrates the skin best and obtains maximum absorption of blood, is the most effective light source, and anticipate that a intensifier tube, CCD, CMOS, etc. may be used as a detector.

In addition, PCT/US2004/005669 filed by Luminetx Corporation discloses a device for facilitating diffusion of infrared light so as to provide uniform illumination. Said device has a complex light source structure to induce the diffusion of infrared light and induce scattered reflection to distribute light uniformly. However, the device not only involves a complex manufacturing process, but also poses a structural obstacle in the manufacture of a product due to its structure.

In addition, devices according to conventional technology can display a life-size image only, and thus it is difficult to see capillaries while using them. In addition, the devices also have a disadvantage of providing a monochromatic image only.

DISCLOSURE OF INVENTION

Technical Problem

The present invention was conceived to solve said problems of conventional technology. An objective of the present invention is to provide a device capable of utilizing infrared light with uniform distribution in a wide area based on a simple constitution.

Another object of the present invention is to provide an image from which noise due to external light sources, such as sunlight, a lamp in the room, etc., was efficiently removed.

A further object of the present invention is to provide a system for obtaining enlarged images at various enlargement ratios and natural color images.

Technical Solution

The objects of the present invention can be achieved by providing a hypodermic vein detection imaging apparatus comprising a dome-shaped holder, a plurality of infrared light sources arranged at a uniform interval in a circumferential direction on the inner surface of the dome-shaped holder, a motor driving unit for rotating the dome-shaped holder, teeth meshing with the motor driving unit and formed on the dome-shaped holder, an optical zoom lens positioned at the center of the top of the dome-shaped holder, an infrared transmitting filter for filtering light transmitted from the optical zoom lens, a first CCD digital camera receiving light filtered by the infrared transmitting filter, and an image display device for visualizing the digital image information obtained by the first CCD digital camera.

The present invention may further comprise a processing device comprising a program capable of processing the digital image information obtained by the first CCD digital camera.

The modus operandi of the hypodermic vein detection imaging apparatus with said constitution is as follows:

The infrared light radiated from the infrared sources, such as infrared LEDs, arranged in a circumferential direction on the inner surface of a dome-shaped holder in the shape of a half sphere, is reflected from the skin and sent to a zoom lens. Because the light which passed through the zoom lens passes through an infrared transmitting filter, but the other light cannot pass through the filter, only the infrared image information including the image of a vein can reach a CCD digital camera. The image of a vein converted into digital image information by the CCD digital camera is visualized by a separate image display device, for example, LCD, CRT, etc.

According to said constitution, various infrared radiation devices, including infrared LEDs arranged on the inner surface of the dome-shaped holder, are used as a light source. In addition, an IR (infrared) radiated region with uniform light intensity distribution can be formed by rotating the dome-shaped holder. Because the skin, the object of detection by infrared light, has an uneven surface, it is important to uniformly illuminate the skin thereby to remove noise due to unevenness.

According to said constitution, in order to illuminate the skin tissues, a plurality of infrared light sources are mounted at a certain interval in a circumferential direction on the inner surface of the dome-shaped holder which has the shape of a partial sphere. According to the present invention, the skin tissues are disposed in the center of the sphere and each LED is arranged to be perpendicular to the surface of the sphere so that it is directed towards the center of the sphere, thereby illuminating the skin tissues uniformly. A rail may be installed on the dome-shaped holder to adjust an incident angle as needed. In addition, in order to eliminate the effect caused by the overlap of the illumination areas by adjacent light sources, the holder itself quickly moves in clockwise/anti-clockwise directions, thereby neutralizing the effect of overlap. Such rotation motion is implemented, for example, by a motor, a worm gear, and the teeth formed at the top of the dome-shaped holder. A circuit switches the rotation direction of the motor. A rotation motion where the rotation direction alternates at every quarter turn is more efficient than one direction rotation motion. Most of the noise due to unevenness can be removed by the rotation motion. According to the present invention, an LED with short wavelengths and an LED with multiple wavelengths may be used simultaneously in order to maintain the maximum optical sensitivity.

In addition, according to said constitution of the system of the present invention, after the radiated infrared light is reflected from the skin, the light is filtered by an optical filter before it is detected by a CCD digital camera, and thereby the present invention produces the effect of efficiently removing noise. The transmission wavelengths of said optical filter are adjusted to the wavelengths of multiple LEDs, and thus removing the noise due to external light sources (sunlight, fluorescent lamp, etc.).

The present invention uses an optical zoom lens, and thereby can obtain an optically enlarged image. Unlike a screen enlargement by digital image processing, the present invention enlarges an original image itself by using a lens, and thus can obtain a vivid enlarged image without blurring the image. Due to this characteristic, the present invention makes it possible to clearly detect capillary vessels which are too thin to be identified, etc. In addition, the zoom lens of the present invention may have a shutter therein so as to have the function of adjusting the intensity of the incoming image.

In addition, according to the present invention, image information of a vein is obtained in the form of digital data by a CCD digital camera, and thus it is possible to easily process said information and visualize it in a desired form.

The present invention may further comprise an optical splitter positioned between the optical zoom lens and the infrared transmitting filter, a second CCD digital camera receiving light split and reflected by the optical splitter, and a processing device comprising a program capable of combining black and white image of a vein obtained by the first CCD digital camera and natural color image of the skin obtained by the second CCD digital camera to visualize it on the image display device.

By virtue of said constitution, the present invention can realize natural colors. After the infrared light reflected from an object passes through a lens, the light is divided into infrared light with information of a vein image and visible light with information of natural color images by an optical splitter and an infrared transmitting filter positioned between the optical splitter and the first CCD digital camera, and then said infrared light and visible light are combined to obtain a natural color image where a vein image is enhanced.

According to the present invention, the first CCD digital camera and the image display device are connected by a detachable connecting unit. The connecting unit is formed as a flexible goose-neck type tube, and thereby makes it possible for the device including the dome-shaped holder and the first CCD digital camera to have various angles with respect to the image display device. Thus, according to the present invention, the user can illuminate the skin with infrared light from any desired direction to obtain image information.

In addition, according to the present invention, the image display device is in the form of a goggle which the user is able to wear, and thus is easy to carry and convenient for use.

Advantageous Effects

According to the present invention as described above, particular infrared LEDs are arranged so as to radiate infrared light with uniform luminance, and the reflected infrared light and natural light from external light sources are separated and image-processed, and thereby an image against a natural color background where only the vein image is reinforced can be obtained. In addition, the present invention has an optical enlargement function which conventional technologies do not have, thereby allowing to detect even the tissues of capillary vessels.

Figure 1:
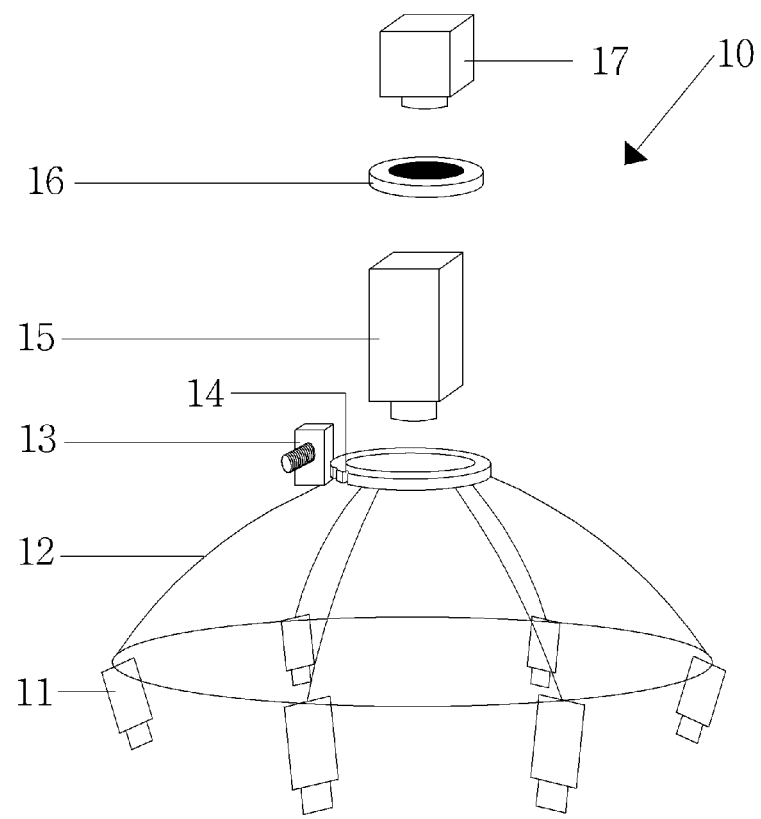
FIG. 1 shows an exploded view of an embodiment of the hypodermic vein detection imaging apparatus according to the present invention.

DESCRIPTION OF MAJOR PARTS IN THE DRAWINGS 10 hypodermic vein detection imaging apparatus
11 infrared LED
12 dome-shaped holder
13 motor
14 teeth
15 optical zoom lens
16 infrared transmitting filter
17 first image detector
18 optical splitter
19 second CCD digital camera
20 image display device
21 connecting unit

BEST MODE FOR CARRYING OUT THE INVENTION

The technical idea of the present invention will be described below, focusing on embodiments according to the present invention. However, the embodiments set forth below are for the purpose of illustration, and the scope of the invention is not in any way limited by the embodiments set forth below.

Embodiment 1

FIG. 1 illustrates an embodiment of the hypodermic vein detection imaging apparatus according to the present invention for detecting hypodermic vein by using a particular infrared LED source and enlarging the image. The system illustrated in FIG. 1 comprises a dome-shaped holder (12), a plurality of infrared LEDs (11) arranged at an uniform interval in a circumferential direction on the inner surface of the dome-shaped holder (12), a motor driving unit (13) for rotating the dome-shaped holder (12), teeth (14) meshing with the motor driving unit (13) and formed on the dome-shaped holder, an optical zoom lens (15) positioned at the center of the top of the dome-shaped holder, an infrared transmitting filter (16) for filtering light transmitted through the optical zoom lens (15), a first CCD digital camera (17) receiving light filtered by the infrared transmitting filter (16), and an image display device (not illustrated) for visualizing digital image information obtained by the first CCD digital camera (17). The optical zoom lens (15), infrared transmitting filter (16), and first CCD digital camera (17) are positioned fixedly in sequence in an upward direction from the dome-shaped holder (12).

In addition, the hypodermic vein detection imaging apparatus according to the present invention may further comprise a processing device comprising a program capable of processing the digital image information obtained by the first CCD digital camera (17).

Figure 2:
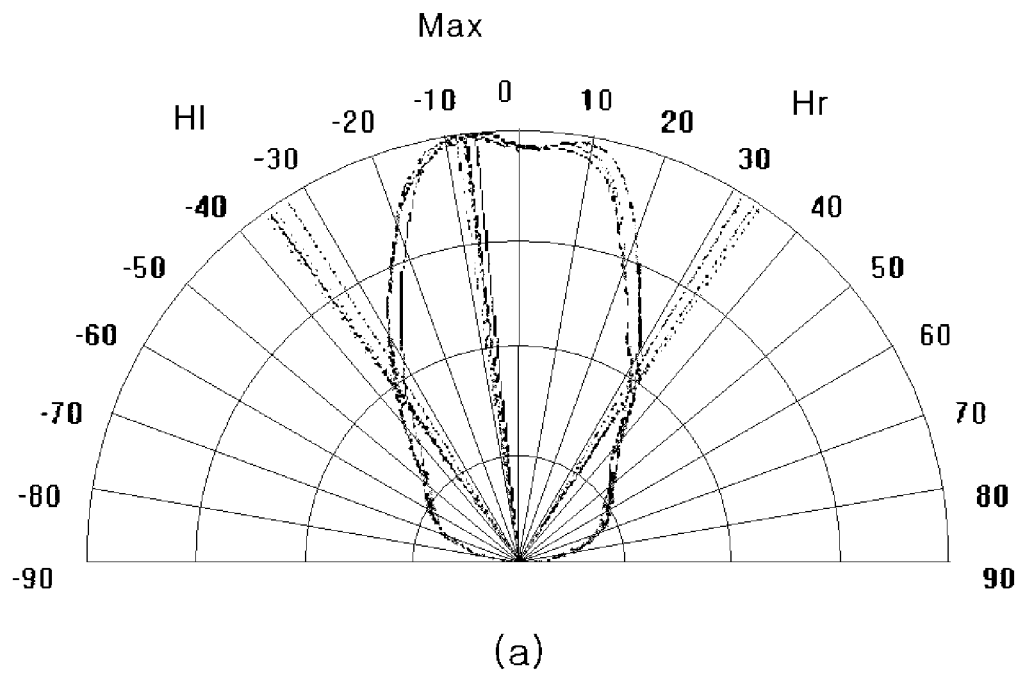
FIG. 2 illustrates the optical characteristic of the infrared LED used in an embodiment of the hypodermic vein detection imaging apparatus according to the present invention.
Figure 2:
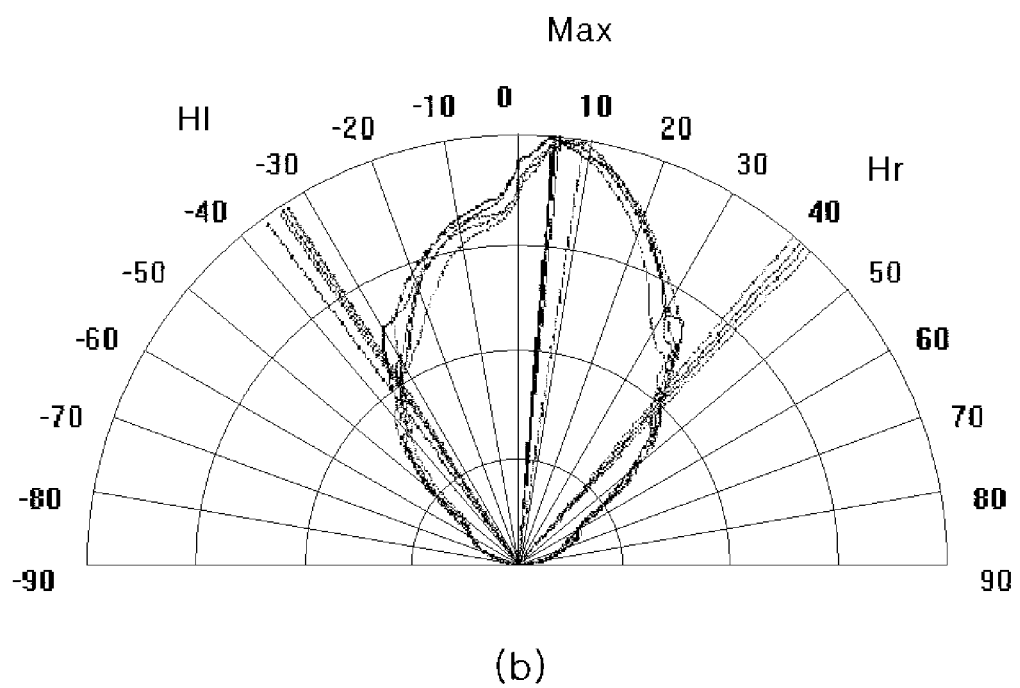

The infrared LED used in the present embodiment has different illumination characteristics than conventional LEDs, and FIG. 2 shows said characteristics. The graph of FIG. 2 shows the distribution of light intensity according to the incident angle of an LED. FIG. 2(a) shows the characteristic curve of the LED used in the present invention, and FIG. 2(b) shows the characteristic curve of a common LED. A conventional, common LED has a light intensity distribution where the light intensity decreases as the incident angle increase to go or decreases to go, whereas the LED used in the present invention has a uniform light intensity distribution regardless of the viewing angle, and thus can remove shadings made due to the unevenness of the skin. In addition, the LED of the present invention can have a plurality of wavelengths arranged therein, and thus can simultaneously radiate a plurality of wavelengths which can optimize the skin penetration depth and the absorbance of blood, without using an additional device. A preferable example of an LED usable for the present invention is Model No. HU1294W manufactured by Knowledge on Inc.

Figure 3:
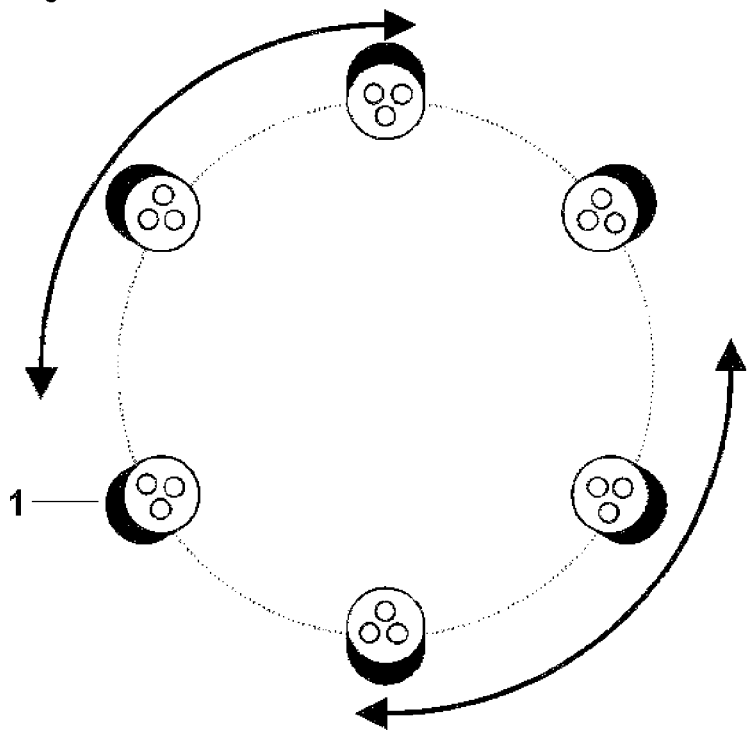
FIG. 3 illustrates the arrangement and movement of infrared LEDs in an embodiment of the hypodermic vein detection imaging apparatus according to the present invention.

FIG. 3 illustrates the arrangement of infrared LEDs on the inner surface of the dome-shaped holder (12) and the rotation of the dome-shaped holder by the motor driving unit (13) and the teeth (14) in the hypodermic vein detection imaging apparatus according to the present embodiment.

Figure 4:
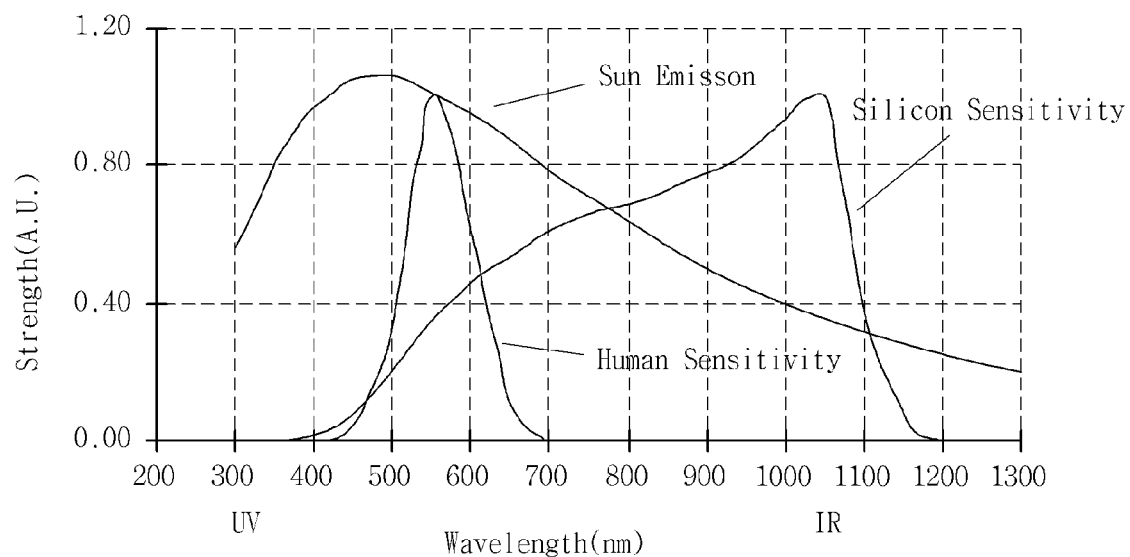
FIG. 4 illustrates general sensitivity of silicone to wavelengths.
Figure 5:
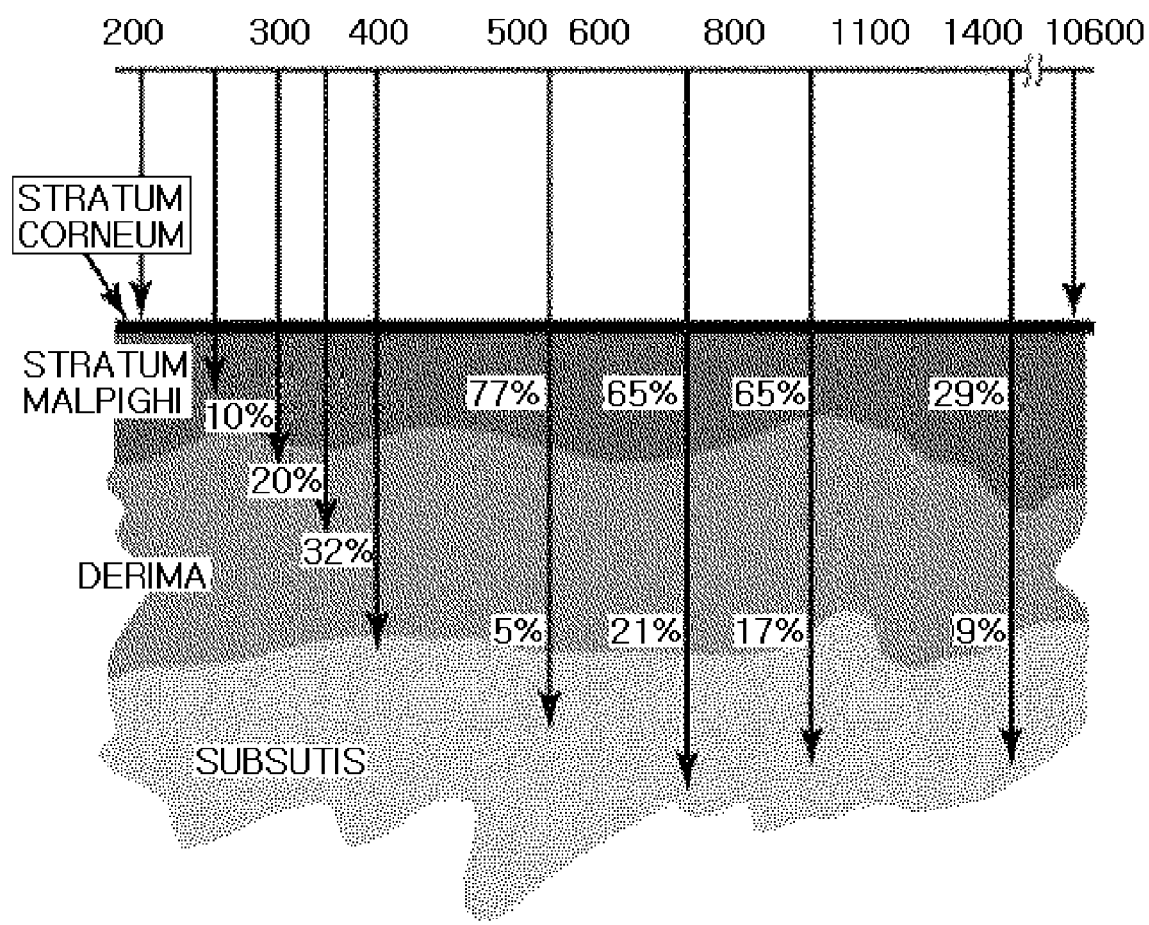
FIG. 5 illustrates the degree of transmission of light through the skin according to wavelengths.

The wavelengths of an infrared LED are determined according to the skin permeation depth, the absorbance of blood, and the sensitivity of a CCD (CMOS) camera. FIG. 4 shows a graph illustrating the sensitivity of silicone (basic material of CCD) to light. In addition, FIG. 5 illustrates skin permeation of light according to the wavelengths. With reference to FIG. 4 and FIG. 5, the optimum wavelengths in terms of the skin permeation depth and the absorbance of blood are in the near-infrared region. In light of this, in the embodiments of the present invention, infrared LEDs with wavelengths of 730 nm and 940 nm are used.

The infrared transmitting filter (16) of the present invention, unlike conventional inventions, is used to prevent the noise made due to external light sources from coming into a detector, not to selectively filter the wavelengths of a light source. Because the infrared LED of the present invention has a narrow wavelength region of 10 nm, and when using a light source with broadband wavelengths such as a lamp, etc., the present invention has the effect of filtering that is necessary to select specific wavelengths, the structure of the present invention provides double filtering effects as a whole. In addition, according to the present invention, an infrared LED enhances the absorbance of blood by specific wavelengths, and an optical filter blocks noise caused due to external light sources, thereby maximizing the definition of an image.

Figure 6:
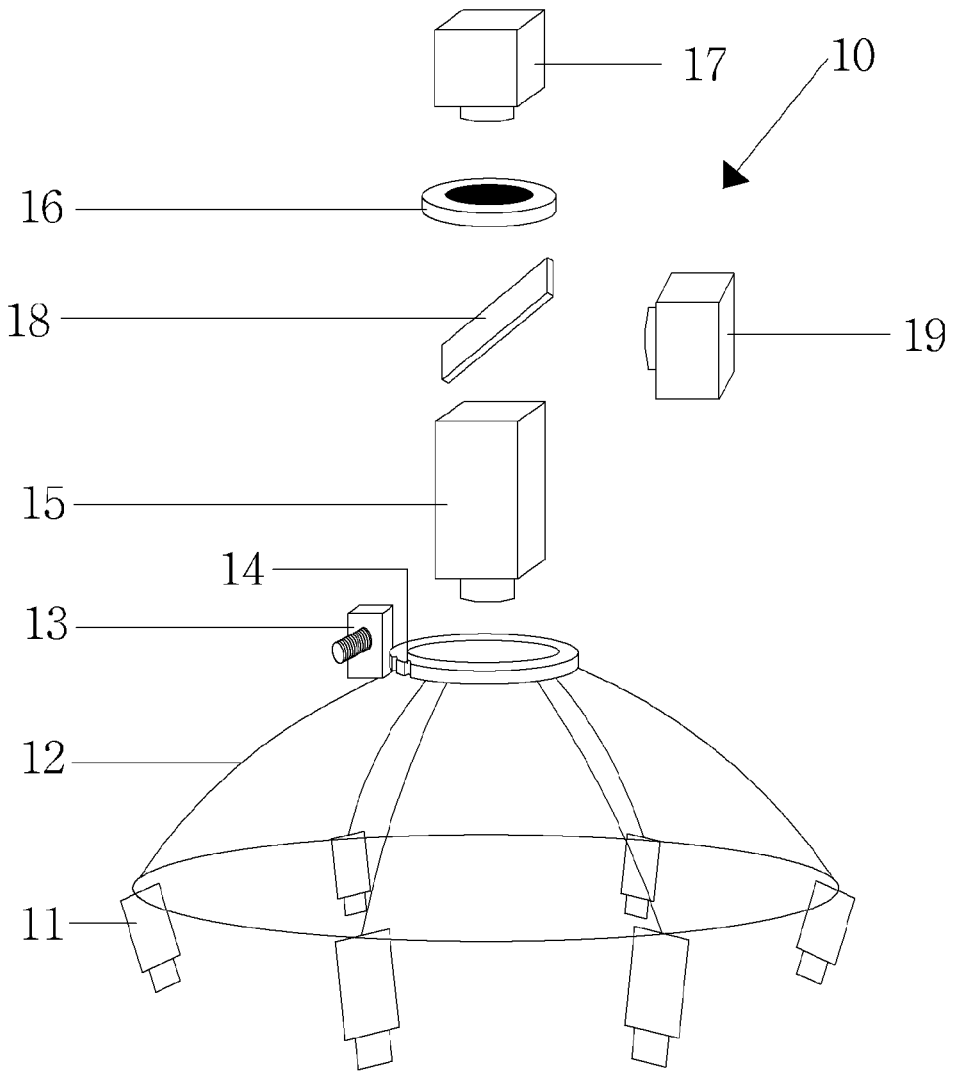
FIG. 6 shows an exploded view of another embodiment of the hypodermic vein detection imaging apparatus according to the present invention.

An embodiment of the hypodermic vein detection imaging apparatus according to the present invention may further comprise an optical splitter (18) positioned between the optical zoom lens (15) and the infrared transmitting filter (16), a second CCD digital camera (19) receiving light split and reflected by the optical splitter (18), a processing device comprising a program capable of combining black and white image of a vein obtained by the first CCD digital camera (17) and natural color image of a skin obtained by the second CCD digital camera (19) to visualize it on the image display device (6). The constitution of said embodiment is shown in FIG. 6.

An image that can be obtained from the embodiment illustrated in FIG. 1 is a black and white image, as from conventional technology. However, the natural colors of actual skin tissues can be obtained by the constitution of the embodiment illustrated in FIG. 6. In the embodiment illustrated in FIG. 6, the second CCD digital camera (19) and the optical splitter (18) are added between the zoom lens (15) and the infrared transmitting filter (16). The reflected infrared light passes through the zoom lens (15), and then the optical splitter (18). Some of the light transmitted through the optical splitter (18) passes through the infrared transmitting filter (16) and is visualized on the first CCD digital camera (17), and some of the light does not pass through the filter and is visualized on the second CCD digital camera (19). The optical splitter (18) is an optical medium which transmits part of the light in the infrared region and reflects part of it, and the ratio of transmission and reflection by the optical splitter (18) can be adjusted. In FIG. 6, some of the light transmitted through the optical splitter (18) passes through the optical filter (16) to make an infrared image, as in the embodiment of FIG. 1, and the light reflected from the filter makes a natural color image directly on the second CCD digital camera (19). In addition, according to the present invention, only the vein structure in the infrared image is overlaid on the natural color image by using software developed by an embodiment of the present invention. High intensity infrared light may exhibit a stronger red color. In such case, an infrared blocking filter may be disposed in front of the second CCD digital camera (19) to modify colors.

Figure 7:
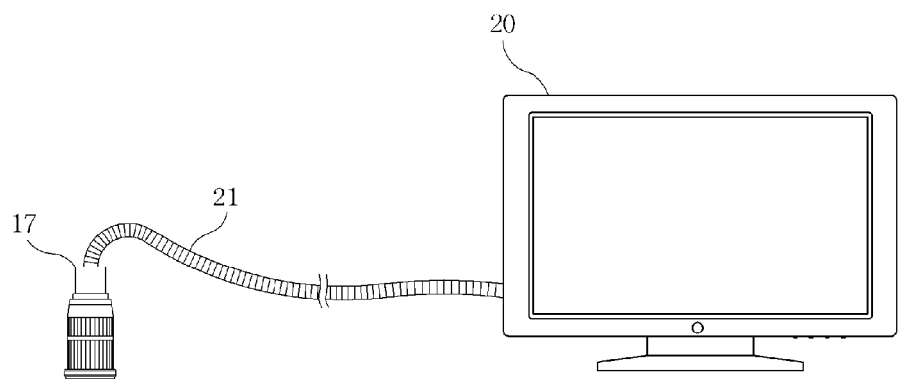
FIG. 7 shows a drawing of another embodiment of the hypodermic vein detection imaging apparatus according to the present invention.

As can be seen from the constitution of the embodiment illustrated in FIG. 7, the first CCD digital camera (17) and the image display device (20) may be connected by a connecting unit (21) in the form of a goose-neck type tube. This connecting unit (21) may be in the form of a conventional goose-neck type tube used for a microphone or a desk lamp. The connecting unit (21) can be formed by inserting a flexible metal rod into a flexible corrugated external tube according to a conventional method. The connecting unit is flexible, and thus can be bent at a desired angle. In addition, the connecting unit can work as a support, and thus can maintain the components being connected at a desired angle. Thus, according to the present invention, the user can maintain the first CCD digital camera (17) and the devices fixed thereto, including the dome-shaped holder (12), the optical lens (15) and the infrared transmitting filter (16), at any desired angle by connecting them to the image display device (20) by the connecting unit (21).

Figure 8:
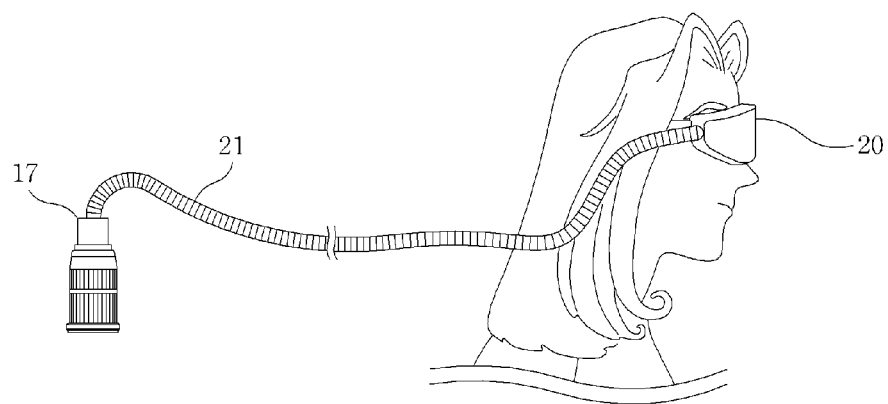
FIG. 8 shows a drawing of another embodiment of the hypodermic vein detection imaging apparatus according to the present invention.

As can be seen from the constitution of the embodiment illustrated in FIG. 8, the image display device (20) may be formed in the form of a goggle which the user is able to wear. Any form of goggle can be used as long as the user can see visualized digital image information while wearing it. Because the image display device (20) is in the form of a goggle, the user can use it while wearing it, and thus the apparatus according to the present invention can be used in various environments and is convenient for use.

Industrial Applicability

The software developed according to the present invention performs the function of processing image information obtained from a CCD camera and visualizing the processed information through a separate image display device. An image is processed by an image processing chip built into the image display device. The image processing chip primarily processes the image information obtained by a CCD camera to remove noise. The location of a vein can be identified more clearly and accurately, when using digitalized vein image information obtained by amplifying a vein image in the image information from which noise was removed. The present invention uses digitalized vein image information, and thus can visualize the vein image in various forms, such as marking the precise location of a vein with a specific line. Thus, the present invention can help identify the location of a vein precisely by using this feature. In addition, the present invention can obtain actual colors and shape of an object being observed by adding various colors to the image, so that the user feels as if he saw an actual vein in the skin.

The invention claimed is:

1. A hypodermic vein detection imaging apparatus comprising
 a dome-shaped holder (12) including teeth (14) formed on the dome-shaped holder's upper surface, a plurality of infrared light source (11) arranged at an uniform interval in a circumferential direction on the inner surface of the dome-shaped holder (12), a motor driving unit (13) for meshing with the teeth (14) so as to rotate the dome-shaped holder (12),
 an optical zoom lens (15), an infrared transmitting filter (16), a first CCD digital camera (17) positioned fixedly in sequence in a direction away from the dome-shaped holder (12), and
 an image display device for visualizing a digital image information obtained by the first CCD digital camera (17).

2. The hypodermic vein detection imaging apparatus according to claim 1, wherein the infrared light sources (11) are LED.

3. The hypodermic vein detection imaging apparatus according to claim 1 or 2, further comprising a processing device comprising a program capable of processing the digital image information obtained by the first CCD digital camera (17).

4. The hypodermic vein detection imaging apparatus according to claim 1 or 2, further comprising
 an optical splitter (18) positioned between the optical zoom lens (15) and the infrared transmitting filter (16),
 a second CCD digital camera (19) receiving light splitted and reflected by the optical splitter (18),
 a processing device provided with a program capable of combining black and white image of a vein obtained by the first CCD digital camera (17) and natural color image of a skin obtained by the second CCD digital camera (19) to visualize it on the image display device.

5. The hypodermic vein detection imaging apparatus according to claim 1 or 2, wherein the first CCD digital camera (17) and the image display device are connected through a detachable connecting unit,
 the connecting unit is formed as a flexible goose-neck type tube.

6. The hypodermic vein detection imaging apparatus according to claim 5, wherein the image display device is the form of goggle which user is able to wear.

* * * * *